US00PP14898P2

(12) United States Plant Patent
Sherman

(10) Patent No.: US PP14,898 P2
(45) Date of Patent: Jun. 15, 2004

(54) PEACH TREE NAMED 'UFBLAZE'

(50) Latin Name: *Prunus persica*
Varietal Denomination: UFBlaze

(75) Inventor: Wayne B. Sherman, Gainesville, FL (US)

(73) Assignee: Florida Foundation Seed Producers, Inc., Greenwood, FL (US)

( * ) Notice: Subject to any disclaimer, the term of this patent is extended or adjusted under 35 U.S.C. 154(b) by 137 days.

(21) Appl. No.: 10/306,707

(22) Filed: Nov. 29, 2002

(51) Int. Cl.[7] ..... A01H 5/00
(52) U.S. Cl. ..... Plt./197
(58) Field of Search ..... Plt./197

*Primary Examiner*—Bruce R. Campell
*Assistant Examiner*—Susan B. McCormick

(57) ABSTRACT

'UFBlaze' is a new and distinct variety of peach tree which has a winter chilling requirement of approximately 300 chill units (cu). The tree is of large size and is highly vigorous with a semi-spreading growth habit. Flowers are showy and pink and leaf glands are small and reniform in shape. Trees of 'UFBlaze' are self fertile and regularly bear heavy annual crops of early season fruit which are large for its ripening season. Fruit are very firm, yellow and non-melting flesh which are clingstone. Fruit are uniform, substantially symmetrical shape, attractive, and have a bright red skin over 80 to 90% of the deep yellow ground color. The fruit usually ripens about 7 to 10 days after 'UFGold' in early to mid-May at Gainesville, Fla.

1 Drawing Sheet

Botanical classification: *Prunus persica.*

BACKGROUND OF THE NEW VARIETY

The present invention relates to a new and distinct variety of peach (*Prunus persica* (L.) Batsch) tree which is named 'UFBlaze' and, more particularly to a peach tree which produces a high percentage of red skin with an attractive deep yellow ground color on the fruit. The fruit is good eating quality with clingstone, non-melting and yellow flesh. Fruit are mature for fresh market in early to mid-May at Gainesville, Fla. Fruit are produced on a tree adapted to a mild winter climate. Contrast is made to 'UFGold' (U.S. Plant Pat. No. 10,315) and 'UF2000' (U.S. Plant Pat. No. 12,019) peach trees for reliable description. This new variety 'UFBlaze' is a promising candidate for commercial success in that it retains fruit firmness at full flavor, tree ripe stage for a week on the tree.

ORIGIN OF THE VARIETY

This peach tree (genotype) originated in a cultivated area of the fruit breeding program at the University of Florida, located at Gainsville, Fla. The seed parent was 'Fla. 90-50CN' (unpatented), a non-melting flesh nectarine [originated as an F2 of (Fla. 84-18C×Fla. 9-20C)] (both unpatented peaches of complex origin). The pollen parent was 'UFGold' peach. UFBlaze was determined to have unique tree and fruit characteristics making it worthy for commercial fresh fruit production. 'UFBlaze' differs from its pollen parent by having fruit of a higher percentage of red skin and ripens one week later and 2 weeks before 'UF2000'. 'UFBlaze' has larger fruit size than 'UFGold', but smaller than 'UF2000', and are produced on a less spreading tree than 'UFGold'. 'UFBlaze' peach tree was selected in 1997, and was designated and tested as Fla. 97-5C. It was asexually reproduced by budding on 'Florda-guard' (unpatented) seedling rootstock at Gainesville, where the selection was made and trees were also tested. Asexually propagated plants remained true to type. There are no known effects of this rootstock on this scion cultivar.

SUMMARY OF THE VARIETY

The new and distinct variety of peach tree bears yellow, non-melting flesh fruit with a high percentage red skin, and has a low chilling endodormancy requirement. 'UFBlaze' peach tree blooms about a week after 'UFGold' peach at Gainesville and the estimated endodormancy requirement is 300 chill units.

The present invention resulting in 'UFBlaze' peach tree is characterized by fruit of excellent flavor and eating quality. The trees are vigorous, productive and without alternate bearing. Trees attain in two years, a height of two and half meters and a spread of two meters at Gainesville. Terminal growth of up to a meter annually is common on mature 4-year old trees with normal pruning to a vase shape. The first fruit ripen in early to mid-May at Gainesville or in about 80 to 85 days from full bloom. The fruit are uniformly large for an early season peach. The skin on ripe fruit has an attractive bright red over a deep yellow ground color. There are some speckles of anthocyanin in the outer flesh on the sun exposed side of the fruit, especially on trees stressed during hot, dry weather. There is no red pigment in the flesh at the pit. The flower anthers are yellow, a common characteristic of many standard peach and nectarine varieties. Flower petals are pink and showy.

DESCRIPTION OF THE DRAWINGS

The accompanying drawing is a color photograph which shows a typical specimen of the fruit, leaf, and stem of the new variety as nearly true as it is reasonably possible to make in a color illustration of this type.

The photograph shows an attractive shape and exterior coloration of six specimens of fruit above a ruler in a stem end view, a blossom end view, side views facing and perpendicular to the suture, and fruits cut longitudinally showing the flesh with and without a pit in place.

DETAILED BOTANICAL DESCRIPTION

The tree, flowers, and fruit may vary in slight detail due to variations in soil type, cultural practices, and climatic condition. The potential for commercial production of fresh fruit by 'UFBlaze' peach tree is high, due to its attractive red skin over a bright yellow ground color, with good flavor balance of sugar and acid, and exceptional firmness due to its non-melting flesh. The present botanical description is that of the variety as grown on 5-year-old trees on 'Florda-guard' rootstock under the ecological conditions prevailing at Gainesville, Fla. Variations of the usual magnitude to changes in climatic growing conditions, soils, fertilization, pruning, irrigation, and pest control are to be expected. Colors (except those in common terms) are described from "The Pantone Book of Color" published by H. N. Abrams, Inc., N.Y. 1990.

Tree:

*Ploidy.*—Diploid.

*Size.*—Trees are large when trained to an open vase form.

*Vigor.*—Vigorous, and must be summer and winter pruned to keep tree height restricted and to keep center of vase open. Trees respond typically to irrigation and fertilization. Tree growth of 5 to 7 feet in height and 4 to 6 feet in width occurs the first growing season in the field. Annual growth on mature trees averages 2 to 4 feet in length.

*Density.*—Medium to dense in branching habit and requires pruning to open the tree center which permits high sunlight entrance for enhancing fruit color and sugar.

*Form.*—Semi-spreading when pruned to vase shape.

*Hardiness.*—Hardy with respect to typical north central Florida winters. Chill units for endodormancy are estimated at 300 cu.

*Bearer.*—Annual and without alternate bearing and must be fruit thinned to avoid limb breakage and obtain large fruit size. Tree annually set several times the number of fruit for a desired crop load.

Trunk:

*Size.*—Large trunk diameter attaining 18 cm diameter at a height of 30 cm above the ground at the end of 5 years growth.

*Bark texture.*—Medium smooth, but changes to medium shaggy as tree ages.

*Bark color.*—Variable with older bark considered mostly gray, Flint Gray (Pantone 16-5803).

*Lenticels.*—Moderate number (18 per 4 square inches of surface area of trunk), small (2–8 mm) with the center being yellowish orange, Golden Ochre (Pantone 16-1346) in late summer.

Branches:

*Size.*—Strong growth of scaffold branches. This is not distinctive of the variety.

*Texture.*—Relatively smooth, medim amout of lenticels attaining size found on trunk and old scaffolds. Roughness increases with age.

*Color.*—New wood is light green, Sweet Pea (Pantone 15-0531) with degree of anthocyanin on the top side (sunny side) relating to intensity of sunlight exposure resulting in a purplish pink, Peach Amber (Pantone 15-1423); Old wood is more brown, Pecan Brown (Pantone 17-1430).

*Crotch angles.*—Angles selected at 45 to 80 degrees in first year of tree training. Natural angles are within the normal range of standard varieties for a semi-spreading tree.

Leaves:

*Size.*—Medium; 14 to 16 cm length, including the petiole; 3.6 to 3.9 cm width. Measurements were made in mid-shoot on vigorous upright summer growth.

*Thickness.*—Regular and average for peach varieties. Not distinctive of the variety.

*Form.*—Lanceolate with an acuminate tip, cuneate base, and serrulate, slightly undulate margin.

*Surface.*—Upper, glabrous; Lower, medium large veins that are pinnately netted.

*Color.*—Lower surface is green, Avocado(Pantone 18-0430); Upper surface is slightly darker green, Mosstone (Pantone 17-0525). Veins on lower surface of old leaves and into the petiole shows only slight anthocyanin development in midsummer to autumn as is typical of a 80 to 85 day peach variety.

*Glands.*—Two to four globose glands mostly on lower leaf blade, but occassionally on petiole. Leaf glands are moderately smaller than those on most commercial varieties. Leaf glands on young leaves are light green, Chartreuse (Pantone 15-0751) on first full size leaves in mid-summer.

*Petiole.*—About 11 mm length; 2.5 mm diameter; Color is light green, Sweet Pea (Pantone 15-031) on young full size leaves of summer.

*Stipules.*—Medium in length (5 to 8 mm), abscising just before the leaf obtains full size, both common to most peach varieties, and 2 per node.

*Arrangement.*—Alternate.

Flower buds:

*Abundance.*—Moderately high, most buds set fruit in absence of spring frosts.

*Size.*—Medium, average 2.5 mm length in late summer.

*Form.*—Plump, conic.

*Surface.*—Pubescent scales.

*Color.*—Brown, Copper Brown (Pantone 18-1336) in late summer.

Flowers:

*Hardiness.*—Hardy with respect to north central Florida winters. No flower bud damage observed during endodormancy at a low of 16F. Flowers have survived when other genotypes of a similar stage of development have failed at freezing temperatures of 25F.

*Blossom period.*—One week after 'UFGold' peach — average February 9–12 at Gainesville, occurring over a 7 to 10 day period, dependant on ambient temperature.

*Aroma.*—Fragrance is slight to none as is normal for most peach varieties.

*Type.*—Showy, location and seasonally variable in size, but within the range of commerical varieties. Average flower diameter — 30 mm. Average petal length, 13 mm; width, 8 mm. Petals are obovate and edges vary from smooth to slightly undulate.

*Color.*—Pink, Orchid Pink (Pantone 13-2010) at flower opening.

*Flower parts.*—Pistil shape and color are within the range of standard commercial varieties. There are 5 sepals and 5 petals, Sepals are pubescent and petals glabrous. Pistils are usually 1 per flower and pubescent. Pistil length (from tip of stigma to base of ovary is 12 mm; Pistil color is light green, Pale Star (Pantone 12-0626). Flower pedicel is 1 to 2 mm length, not distinguishing for the variety.

*Anthers.*—Yellow, Golden Cream (Pantone 13-0939) at flower opening.

*Stamens.*—Number varies from 26 to 35. Length is 7 to 10 mm.

*Pollen.*—Abundant and bright yellow, Pastel Yellow (Pantone 11-0616).

*Calyx cup.*—Medium large (5 mm diameter at the top and 5 mm depth).

*Fertility.*—Self fertile, and no cross pollination is required.

Fruit:

*Maturity when described.*—Tree ripe, May 8, 2002 at Gainesville.

*Date of first picking.*—May 3, 2002 at Gainesville.

*Date of last picking.*—May 13, 2002 at Gainesville.

*Size.*—Uniform, medium large (large size for early mid-season maturity at 100 to 120 g). Varies with number of fruit per tree, soil type, climate and cultural practices.

*Average equatorial diameter.*—2½ inches (63 mm).

*Average polar length* (*stem to distal end*).—2½ inches (61 mm).

*Pedicel.*—Length — 7 to 9 mm; Width — 3 to 4 mm. Color is green, Golden Green (Pantone 15-0636).

*Longitudinal section form.*—Slightly oval.

*Transverse section through diameter.*—Round.

*Suture.*—Inconspicuous in form and color.

*Ventral surface.*—Rounded.

*Base.*—Slightly retuse.

*Apex.*—Round to slightly obtuse.

*Crater at pedicel.*—Flaring circular. Stem depressing on base of fruit. Crater depth is 6 to 10 mm, breadth is 22 mm at top is 3 mm at pedicel attachment.

Skin:

*Thickness.*—Medium, not a distinguishing feature.

*Texture.*—Medium short pubesence, similar to that of UFGold peach.

*Tenacity.*—Tenacious to flesh.

*Color.*—Bright red, Fire Cracker (Pantone 16-1452) over 60 to90% of the skin with darker red vertical stripes, Aurora Red (Pantone 18-1550) at first harvest. Ground color is deep yellow, Radiant Yellow (Pantone 15-1058). Fruit exposed to the sun have a higher degree of enhanced red skin.

*Tendency to crack.*—None observed.

*Taste.*—No astringency observed.

*Pubescence.*—Short, medium soft to touch.

Flesh:

*Ripens.*—Evenly within each fruit and throughout the tree.

*Texture.*—Firm, fine, juicy, non-melting when fully ripe.

*Fibers.*—Very fine, small, tender, and abundant throughout the flesh.

*Aroma.*—Moderate and in the middle range of commercial peach varieties.

*Eating quality.*—Good, sweet, slightly acid. Fruit averaged near 12 brix when described. Titratable acidity was 0.88 as % malic acid and penetrometer firmness at harvest was 1.4 kg with a standard 8 mm tip.

*Juice.*—Abundant.

*Color.*—Deep yellow, Saffron (Pantone 14-1064) with a small amout of red, Hot Coral (Pantone 17-1656) throughout the flesh on stressed trees, especially under dry, hot conditions. There is no red at the pit.

*Browning by oxidation.*—Slight on tree ripe fruit beginning to soften.

*Amygdalin.*—Undetected.

Stone:

*Type.*—Clingstone, adhering to flesh even at softening.

*Size.*—Mediun small; average length is 30 mm; average diameter at the equator perpendicular (dorsal to ventral side) to the suture is 23 mm; average thickness at the equator across (facing) the suture is 18 mm; average wall thickness at the equator perpendicular to the suture is 5 to 6 mm.

*Color.*—Light brown, Wheat (Pantone 13-1016) when freshly exposed.

*Form.*—Elliptic shape with an acuminate tip and acute base.

*Sides.*—Near equal.

*Surface.*—Irregularly furrowed toward the ventral edge, pitted from the center toward the base and apex.

*Ridges.*—Jagged toward the base.

*Tendency to split.*—None observed.

*Kernel.*—Oval shape, bitter (amygdalin is abundant) and viable, germinating only with embryo culture. Average width, 9 mm; average length 13 mm; Color is light brown, Golden Ochre (Pantone 161346) when first removed from fresh fruit.

Use: Fresh; dessert.

Resistance to disease: High resistance to bacterial spot incited by *Xanthomonas campestris* pv. *pruni.* Resistance to other fruit and tree diseases are within the range for commercial peach cultivars in Florida. No unusual resistance or susceptibility or insects and diseases noted.

Keeping quality: Excellent after 2 weeks at 35F and with minimal bruises or scarring appearing on skin.

Shipping quality: Degree of firmness at harvest and firmness retained in refrigeration for 2 weeks at 7C with no internal breakdown of flesh or appreciable loss of eating quality indicates fruit should be highly acceptable for shipping.

I claim:

1. A new and distinct peach tree variety as illustrated and described, characterized by a low chilling requirement, and bearing early season fruit having firm, yellow and non-melting flesh of high eating quality, and an attractive, high percentage red skin color with fruit ripening in early to mid-May or about 7 days after 'UFGold' at Gainesville, Fla.

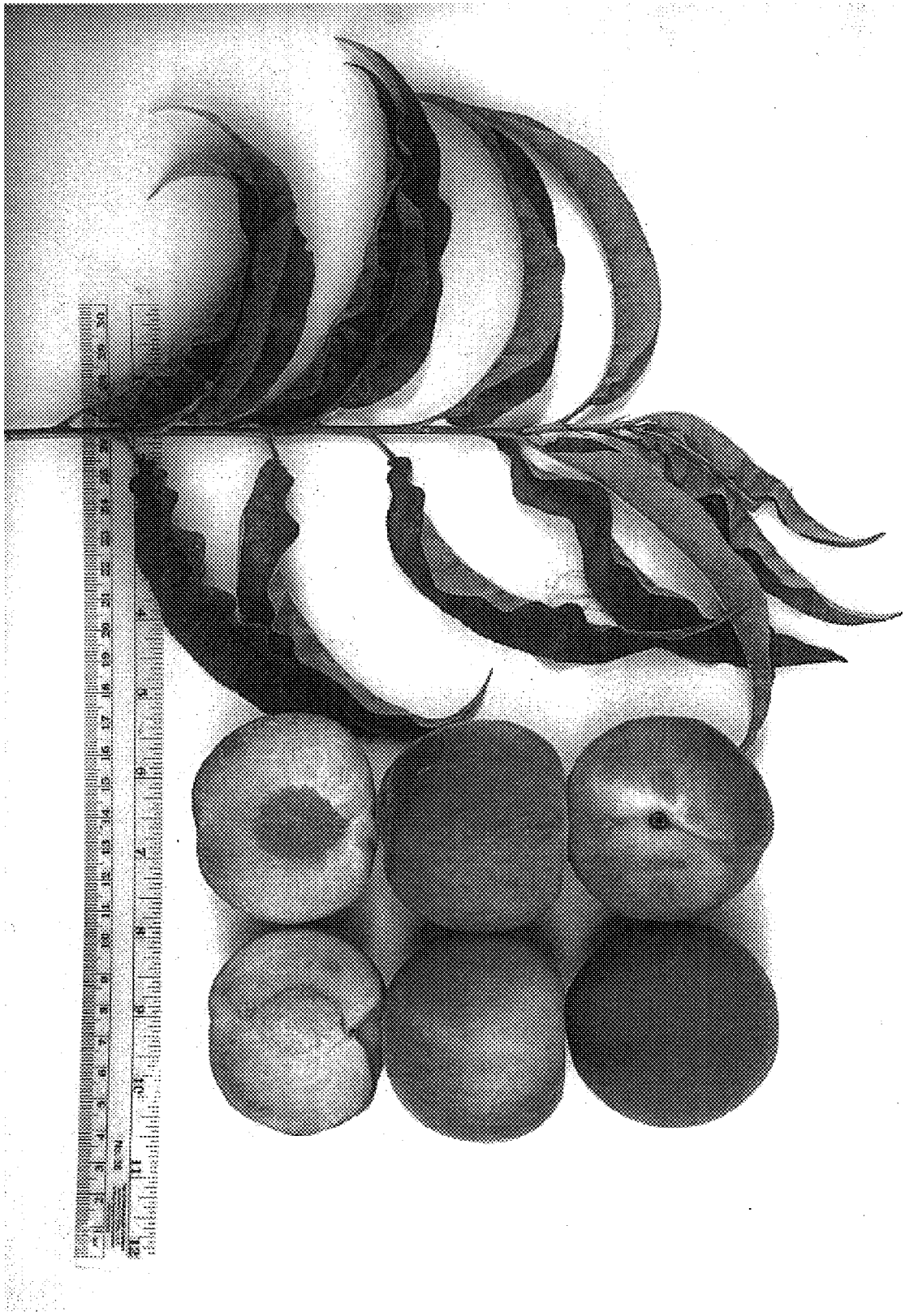

* * * * *